US007011852B2

(12) United States Patent
Sukavaneshvar et al.

(10) Patent No.: US 7,011,852 B2
(45) Date of Patent: Mar. 14, 2006

(54) SEPARATION OF PLATELETS FROM WHOLE BLOOD FOR USE AS A HEALANT

(75) Inventors: Sivaprasad Sukavaneshvar, Salt Lake City, UT (US); S. Fazal Mohammad, Salt Lake City, UT (US)

(73) Assignee: Hemogenesis, LLC, Salt Lake City, UT (US)

( * ) Notice: Subject to any disclaimer, the term of this patent is extended or adjusted under 35 U.S.C. 154(b) by 361 days.

(21) Appl. No.: 10/141,626

(22) Filed: May 6, 2002

(65) Prior Publication Data

US 2002/0179537 A1    Dec. 5, 2002

Related U.S. Application Data

(60) Provisional application No. 60/289,224, filed on May 7, 2001.

(51) Int. Cl.
    *A61K 35/14*    (2006.01)

(52) U.S. Cl. ..................................... 424/532
(58) Field of Classification Search ................. 424/532
    See application file for complete search history.

(56) References Cited

U.S. PATENT DOCUMENTS

| | | | |
|---|---|---|---|
| 3,900,290 A * | 8/1975 | Hornstra | ................. 73/61.73 |
| 4,269,718 A | 5/1981 | Persidsky | |
| 4,760,131 A | 7/1988 | Sundsmo et al. | |
| 5,165,938 A | 11/1992 | Knighton | |
| 5,599,558 A | 2/1997 | Gordinier et al. | |
| 5,733,545 A | 3/1998 | Hood, III | |
| 5,788,662 A | 8/1998 | Antanavich et al. | |
| 5,834,418 A | 11/1998 | Brazeau et al. | |
| 5,858,253 A | 1/1999 | Holm | |
| 6,063,624 A | 5/2000 | Kandler et al. | |
| 6,071,423 A | 6/2000 | Brown et al. | |
| 6,197,598 B1 | 3/2001 | Schrier et al. | |
| 6,214,338 B1 | 4/2001 | Antanavich et al. | |
| 6,221,575 B1 | 4/2001 | Roser et al. | |
| 6,303,112 B1 | 10/2001 | Worden | |
| 6,326,197 B1 | 12/2001 | Kandler et al. | |
| 6,398,972 B1 | 6/2002 | Blasetti et al. | |

FOREIGN PATENT DOCUMENTS

| | | |
|---|---|---|
| EP | 0 417 818 A1 | 3/1991 |
| JP | 411246420 | 9/1999 |

OTHER PUBLICATIONS

Stimulation of Repair in Chronic Nonhealing, Cutaneous Ulcers Using Platelet-Derived Wound Healing Formula, David R. Knighton, et al., *Surgery, Gynecology & Obstetrics*, Jan. 1990, vol. 170.
Current Concepts in Wound Healing: Growth Factor and Macrophage Interaction, Douglas T. Cromack, et al. *Advances in Understanding Trauma and Burn Injury*, vol. 30, No. 12-Supplement.
Involvement of Platelets in Stimulating Osteogenic Activity, Michael Slater, et al., *Journal of Orthopedic Research*, vol. 13, No. 5, 1995.
Characterization of Human Platelets Separated From Blood by ADP-Induced Aggregation, S. Fazel Mohammad, et al., *American Journal of Pathology*, vol. 79, No. 1, Apr. 1975.
Platelet Concentrates in an Additive Solution Prepared From Pooled Buffy Coats, Lars Eriksson, et al., *Vox Sang*, 1990; 59:140-145.
Storage of Platelets in Additive Solutions: A New Method for Storage Using Sodium Chloride Solution, , H. Gulliksson, et al., *Transfusion*, vol. 32, No. 5, 1992.

* cited by examiner

*Primary Examiner*—Jean C. Witz
(74) *Attorney, Agent, or Firm*—Thorpe North & Western, LLP

(57) ABSTRACT

A method is described for separating, retrieving and concentrating platelets from whole blood relying on aggregation of the platelets followed by filtration. This method eliminates the need of a centrifuge for separating said cells from blood. To obtain cellular concentrates of platelets, blood is mixed with compatible agents that will aggregate cells while retaining contained growth factors. The resulting aggregates can then be separated from blood by filtration. If desired, the filter-captured aggregates are subject to a brief washing cycle where they are washed clean of residual aggregating agent, plasma, and red cells. Aggregates can then be partly or wholly deaggregated and the cells retrieved. The result is a suspension of cells and small aggregates with therapeutic levels of concentrated blood cells with included growth factors that are available for delivery to a wound site. A device that accomplishes the aforementioned process is also described.

28 Claims, 3 Drawing Sheets

SEPARATION OF PLATELETS FROM WHOLE BLOOD FOR USE AS A HEALANT

This application claims the benefit of U.S. Provisional Application No. 60/289,224 filed on May 7, 2001.

FIELD OF THE INVENTION

The present invention relates to wound healants, as well as systems, methods, and devices for harvesting growth factors. More specifically, by separating platelets from whole blood, growth factor rich platelets can be harvested, concentrated, and delivered for wound healing in accordance with embodiments of the present invention.

BACKGROUD OF THE INVENTION

An attractive emerging clinical approach for augmenting wound healing is the rapidly expanding clinical and surgical use of recombinant or autologous growth factors for improved therapeutic outcomes. Examples of areas where such wound healing compositions are useful include intractable decubitus and pressure ulcers; orthopedic bone defect repair and bone ingrowth in fixation and implantation procedures; plastic and maxillofacial surgery; burn skin grafts; connective tissue repair; periodontal surgery, etc., as described by: Knighton D R, *Surgery, Gynecology & Obstetrics* 170: 56–60. 1990; and in Slater M, *J Orthop Res* 13: 655–663. 1995. The widespread clinical and surgical acceptance of growth factor-based wound healing therapies are currently limited to some degree by the high cost associated with both recombinant and autologous growth factor healants, and the additional inconvenience of processing autologous cells intraoperatively. Although only few controlled comparisons have been made between autologous growth factor cocktails and purified protein recombinant growth factors for wound healing effectiveness, a single recombinant growth factor may be less effective in many wound healing applications than a combination of natural growth factors (PDGF, VEGF, TGF, EGF, etc.) present in platelets as suggested by Cromack D T, *J Trauma*. 30: S129–S133, 1990. To that end, several potentially therapeutic growth factor compositions have been developed that contain more than one growth factor. However, the clinical applicability of some of these healants can be limited by high cost and inconvenience of obtaining growth factor compositions for use.

The process described herein would allow for a cost effective, timely, and convenient technique for isolation and concentration of autologous or homologous platelets with included active growth factors. These cells may be harvested from small volumes of patient blood preoperatively, intraoperatively, perioperatively, or for outpatient procedures to allow for convenient and sustained delivery of growth factors to effectively promote healing. Current autologous growth factor harvesting systems are expensive and rely on technician-intensive blood processing to generate platelet rich plasma (PRP) prior to the additional steps required to harvest platelets to desired therapeutic concentrations, e.g., by centrifugation, by gel filtration, or by ultrafiltration. Laboratory separation by gravity has also been used, though time constraints makes this a less desirable approach.

SUMMARY OF THE INVENTION

It has been recognized that providing a wound healant using systems, methods, and devices to rapidly, conveniently and cost-effectively harvest platelets from whole blood using aggregation of platelets followed by filtration of those aggregates and appropriate retrieval would be an advancement in the area of accelerated wound healing. Such autologous platelet harvesting methods and systems can enable the elimination of the use of a centrifuge that can be expensive, inconvenient to operate, and can be more time consuming to use than the use of the systems, methods, and devices of the present invention.

With this in mind, a method for separating platelets from whole blood can comprise the steps of (a) providing whole blood including platelets, leukocytes, erythrocytes, and blood plasma; (b) selectively aggregating platelets using an aggregating agent to form platelet aggregates that are larger in size than said leukocytes and erythrocytes; and (c) substantially separating the platelet aggregates from the leukocytes, erythrocytes, and blood plasma. Alternatively, a method for separating platelets from a platelet suspension can comprise the steps of (a) selectively aggregating platelets using an aggregating agent to form platelet aggregates in a platelet suspension where the aggregation function of platelets is realizable; and (b) separating the platelet aggregates from platelet suspension by filtration. The platelet suspension can be whole blood, platelet rich plasma, or a platelet pack, for example.

In either of the above embodiments, the platelet aggregates obtained can then be washed, deaggregated, and/or suspended after separating, such as by filtration, in a desired solution. In one embodiment, the platelet aggregates can be deaggregated and concentrated to a desired therapeutic level for delivery to a wound site. Further, though centrifugation is not precluded by the present method, in a preferred embodiment, the platelets can be separated without the use of centrifugation. Additionally, the step of selectively aggregating the platelets can be enhanced by mixing the whole blood and the aggregating agent at a temperature from 20° C. to 37° C. for about 60 to 180 seconds.

Many aggregating agents can be used in accordance with the present invention, including aggregating agents selected from the group consisting of thrombin, ristocetin, arachidonic acid, collagen, epinephrine, adenosine diphosphate, and combinations thereof. A preferred aggregating agent for use is adenosine di-phosphate (ADP).

In a more detailed aspect of the present invention, the platelets can be washed with a desired salt solution at a temperature from about 18° C. to 30° C. and for about 1 to 3 minutes to remove residual components including agonists, red blood cells, and plasma proteins. In another more detailed aspect, an additional step can be carried out that includes gently agitating/aspirating the aggregated platelets after separation with an appropriate solution to deaggregate and resuspend the platelets while minimizing degranulation, thereby recovering single cells and/or small cell aggregates. With this embodiment, the agitation/aspiration step can occur under controlled temperatures from 33° C. to 37° C., and at a pH from about 6 to 8.

Once the platelets are collected, they can be applied to a wound, target tissue, or cells by any of a number of methods. For example, the step of filtering can be conducted with a biodegradable filter that can be placed directly on a wound site. Such a biodegradable filter can comprise a material selected from the group consisting of polyglycolic acid, polylactic acid, polypeptides, collagen, hyaluronic acid and combinations thereof. Alternatively, suspended cells can be placed directly on a wound site, such as by a direct application, a poly-glycolic acid patch, a polyester patch, or a gel seal suture. Furthermore, platelets can be mixed with plasma, gelatin, fibrin/fibrinogen, alginates, chitosan or other sponges, bone fillers such as calcium phosphate, or other similar clinically accepted wound dressing/filling substrates.

One additional aspect of the present invention that is desirable is the fact that autogolous treatment can occur within 15 minutes or less following blood collection. This is particularly useful for emergency reinfusion or transfusion of platelets. This is also useful in operating room settings where time is often critical during surgical procedures in which a wound healant is desired for use.

In another embodiment, a device for separating platelets from whole blood can comprise a mixing/filtering chamber configured for mixing whole blood and an aggregating agent when positioned in a first orientation, and further configured for filtering platelet aggregates formed during mixing when positioned in a second orientation. The device can also contain an inlet or multiple inlets for transferring whole blood and the aggregating agent into the mixing/filtering chamber (together or separately), and washing the aggregates. The device can also comprise a mixing mechanism for mixing the whole blood and the aggregating agent when the mixing/filtering chamber is positioned in the first orientation, and a filter for collecting the platelet aggregates when the mixing/filtering chamber is positioned in the second orientation. One or more outlet ports can also be present for removing residual components of the whole blood that are not collected on the filter, and to provide a means to access, deaggregate and harvest the aggregates captured on the filter. In one embodiment, the mixing mechanism can be configured to optimize mixing, and to prevent substantial premature release of growth factor contents from the platelets, e.g., by means of a magnetic stirrer.

In an alternative device embodiment, a device for separating platelets from whole blood can comprise a mixing chamber configured for receiving and mixing whole blood and an aggregating agent to form platelet aggregates and residual blood components. A filtering chamber can be configured for collecting platelet aggregated in the mixing chamber and allowing the residual blood components to substantially pass, wherein the filtering chamber comprises a porous filter. A valve can be placed between the mixing chamber and the filtering chamber for holding the whole blood and the aggregating agent in the mixing chamber during mixing, and for allowing flow of the platelet aggregates and the residual blood components from the mixing chamber in to the filtering chamber to separate aggregates from blood. Additionally, an outlet or filter port can be present and configured for removing components of the whole blood that are not collected in the filter.

The filter used in either of the above device embodiments can be made of single or multiple stages of filters with a pore size ranging from 15 to 500 $\mu$m, though a more preferred pore size can range from 15 to 100 $\mu$m. In one embodiment, the filter can comprise a material selected from the group consisting of metals, polymers, biomaterials, biodegradable materials, and combinations thereof. In more detail, the filter can comprise a material selected from the group consisting of stainless steel, nylon, poly-tetra-fluoro-ethylene (Teflon), polyester, and/or hyaluronic acid. The outlet port can also act as an inlet port for injecting a physiological medium for washing and/or for injecting a deaggregating agent, though this is not required. In further detail with respect to preferred structures, the mixing device can comprise an electromagnetic motor and a magnetic stir bar.

In still another embodiment, a wound healant for human tissue can comprise a physiological solution, essentially free of thrombin or other degranulating agents, autologous platelets suspended in the physiological solution; and a clinical carrier substrate configured for carrying the platelets to a wound site. Such a solution is merely one possible composition that can be prepared in accordance with the methods of the present invention. However, this composition can be desirable for use because wound treatment can be effected without the step of adding a degranulating agent, e.g., thrombin, that are typically used in the art.

Alternatively, a wound healant for application to tissue can comprise a combination of platelet aggregates and single platelets, wherein the platelet aggregates and the single platelets are suspended in a physiological solution and carried by a clinical carrier substrate. An advantage of utilizing such a combination includes the possibility that aggregated platelets may provide immediate release of growth factor to a tissue, whereas individual, non-aggregated platelets may provide growth factor to a tissue site over time. Therefore, such a wound healant can provide immediate growth factor treatment to a tissue, as well as provide some sustained release of growth factor over time.

In either of the above embodiments, substantially intact platelets can be delivered directly in, for example, a physiological solution such as isotonic saline solutions. In one embodiment of such a wound healant, the autologous platelets with contained growth factors can be present at a concentration greater than three times normal levels compared to that present in blood, wherein the platelet is not substantially activated by degranulating agents such as thrombin. Further, the physiological solution that acts as the wound healant can be essentially free of serum or plasma proteins.

As described herein with respect to a process of the present invention, the platelets can be prepared and be present as single cells or small aggregates of cells that are distributed within a clinical carrier substrate, thereby providing a dispersed and prolonged release of growth factors. The healant can be delivered as suspended cells in a physiological solution, in a patch such as a poly-glycolic acid patch, a polyester patch such as a Darcon patch, or as a gel such as part of a gel suture system. Additionally, such a wound healant can also be combined with a hemostatic sealant to contribute growth-promoting properties of the wound healant. Further, such a wound healant can also be incorporated into aneurysm substrates or fillers such as coils or gels to accelerate the healing and/or re-integration of an aneurysm.

BRIEF DESCRIPTION OF THE DRAWINGS

In the accompanying drawings which illustrate embodiments of the invention.

DETAILED DESCRIPTION OF THE PREFERRED EMBODIMENT(S)

Figure 1:
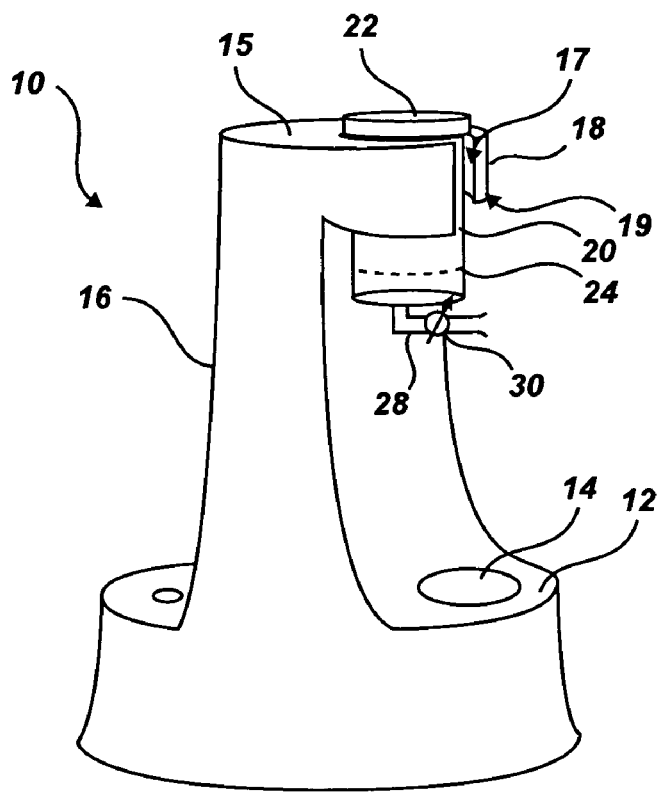
FIG. 1 is a perspective view of a system in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention. It is also to be understood that this invention is not limited to the particular configurations, process steps and materials disclosed herein as these may vary to some degree. It is also to be understood that the terminology used herein is used for the purpose of describing particular embodiments only, and is not intended to be limiting as the scope of the present invention.

It must be noted that, as used in this specification and the appended claims, singular forms of "a," "an," and "the" include plural referents unless the content clearly dictates otherwise.

"Physiological solution" or "physiological medium" can be saline, plasma, or other isotonic salt solutions.

As illustrated in FIG. 1, a system, indicated generally at 10, in accordance with an embodiment of the present invention is shown. In accordance with one aspect of the present invention, the system 10 provides a base 12 and a well 14 within the base. Extending upwardly from the base 12 is a longitudinal support 16 terminating in a flat upper surface 15 containing an aperture 17 defined by support 16 and a pair of partially encircling arms 18. Aperture 17 is configured for holding cylindrical mixing/filtering chamber 20.

The cylindrical mixing/filtering chamber 20 has an enclosed expanded end consisting of a flange 22. The flange 22 is larger than the diameter of aperture 17 such that when chamber 20 is inserted into aperture 17 in an inverted filtering or separating position, as shown, the flange 22 will rest on flat surface 15. A space 19 between arms 18 is provided to enable a syringe 44 (not shown) or other device attached at the opposite end of mixing chamber 20 to pass between space 19 when the mixing chamber is inserted into or removed from aperture 17. The well 14 is also configured to hold the mixing chamber 20 at the flanged end 22. Specifically, the flanged end 22 of the mixing/filtering chamber 20 can be placed in the well 14 in a mixing position (not shown). In this position, the mixing/filtering chamber 20 is in position for gently mixing the whole blood. Thus, the system 10 provides a means of fixing the mixing/filtering chamber 20 in both a filtering position as shown, and in a mixing position (not shown).

The mixing/filtering chamber 20 is described in greater detail hereinafter. FIG. 1 shows a filter 24 for filtering aggregated blood cells, a stem 28 for removing and adding fluids, and a valve 30 for starting and stopping fluid flow. With respect to the mixing/filtering chamber 20, the outside surface of the cylindrical walls can contain tongues and/or grooves (not shown) and arms 18 can likewise contain matching grooves and/or tongues (not shown) such that, when the mixing device is inserted in aperture 17, it will be locked in a tongue in groove non-rotating position. Likewise, a similar system can be present where the mixing/filtering chamber 20 rests in the well 14.

Figure 2:
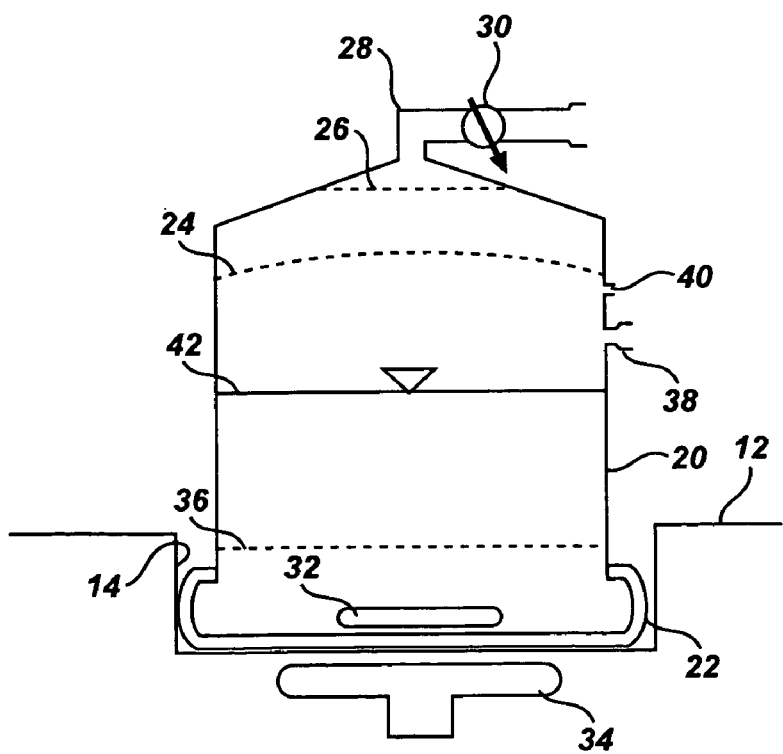
FIG. 2 is front view of a mixing/filtering chamber of the system of FIG. 1, and is configured in the mixing position.

In FIG. 2, the mixing/filtering chamber 20 is shown in a mixing position. Specifically, the flanged end 22 is shown resting snugly in the well 14 of the base 12. A filter 24, a filter grid 26, and an outlet stem 28 are shown, but are not typically in use when the mixing/filtering chamber is in the mixing position shown. A port 38 is present for transferring whole blood and/or aggregating agent into the mixing/filtering chamber 20. A pressure-reducing vent 40 is also present for allowing air to escape when displaced by the transfer of whole blood into the mixing/filtering chamber 20. Both the vent 40 and the port 38 can be equipped with stoppers or valves for preventing the outflow of whole blood when the mixing/filtering chamber 20 is in the filtering position. Though only one port and one vent are shown, it is understood that multiple ports and/or vents may be present. For example, separate ports can be used for transferring whole blood and aggregating agent into the mixing/filtering chamber. Alternatively, the whole blood and aggregating agent can be mixed prior to insertion into the mixing/filtering chamber 20. Furthermore, the aggregating agent may be predispensed in the mixing/filtering chamber prior to addition of blood.

Once the whole blood and aggregating agent are present in the mixing/filtering chamber 20 at a desired blood level 42, a magnetic stir bar 32 can be rotated at flanged end 22 using a motor magnet 34 controlled by a microprocessor (not shown). A Peltier chip for temperature control and timer-alarms can also be present within base 12 or longitudinal support 16, if desired. In the embodiment shown, the motor magnet 34 is located at the bottom of well 14. Any other stirring or mixing configuration can also be used that is gentle enough to mix the whole blood with an aggregating agent without substantially damaging or degranulating platelets, but vigorous enough to thoroughly mix the aggregating agent with the whole blood. A stir bar grid 36 is also present to prevent the stir bar 32 from falling onto the filter 24 when the chamber 20 is inverted as shown in FIG. 3.

Figure 3:
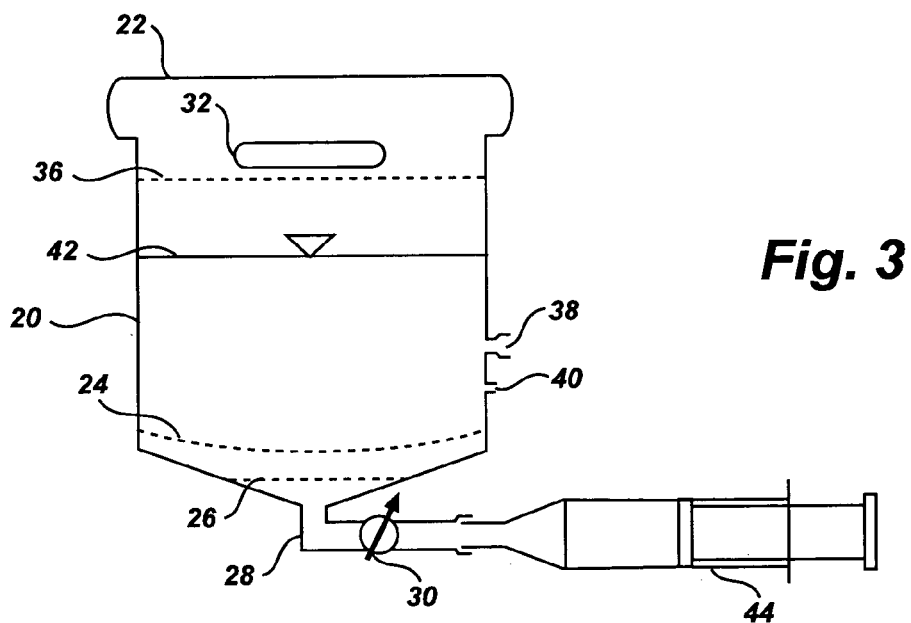
FIG. 3 is front view of a mixing/filtering chamber of the system of FIG. 1, and is configured in the separating position.

Referring now to FIG. 3, the mixing/filtering chamber 20 is shown in a filtering position. The mixing/filtering chamber 20 is held in this position as the chamber is inserted in aperture (not shown) with flanged end 22 resting on flat surface (not shown). The stir bar 32 is prevented from falling into the aggregated whole blood by the stir bar grid 36.

The filter 24, filter grid 26, stem 28, valve 30, and a syringe 44 are now rendered useful with the mixing/filtering chamber 20 in the position shown in FIG. 3. Specifically, whole blood is drawn through the filter 24 by creating negative pressure by opening valve 30 and partially withdrawing the plunger of syringe 44. Though a syringe is shown, any pump device can be used. The filter 24 can include one or more filters with nominal pore-sizes ranging from 15 to 500 $\mu$m. Further, the filter can be designed to capture aggregated platelets while allowing the passage of non-aggregated cells, e.g. red blood cells and leukocytes, residual aggregating agent, and plasma. The filter can also consist of a removable biodegradable filter, which can be configured to capture aggregates, and be applied directly (after washing if desired) to the wound site with little or no further processing.

A filter grid 26 can be present to prevent the filter 24 from getting too close to the stem 28, thus maintaining a larger surface area of filter 24 functional for its intended purpose.

The filter 24 has large enough pores to allow non-aggregated blood cells through, but small enough pores to prevent aggregated platelets from passing. Thus, aggregated platelets can be trapped on the filter, and substantially all of the plasma, leukocytes, and red blood cells can be removed.

Referring generally to FIGS. 1 to 3, platelet concentrates prepared according to the methods and systems described herein can be prepared by transferring a desired volume of blood to the mixing/filtering chamber via an infusion port 38 to attain a desired blood level 42. Inside air can be vented through an air vent 40. An aggregating agent can either be present when the blood is transferred to the chamber, or can be placed with the blood once in the chamber. The aggregating agent and the whole blood can now be manually, semi-automatically, or automatically mixed. It is to be noted that the chamber in which mixing is accomplished is designed to effectively induce platelet aggregation in whole blood without releasing bound growth factors. Thus, mixing should occur that is gentle enough to reduce the release of growth factors, and vigorous enough to promote adequate aggregation. A stable and relatively fixed, rigid, semi-rigid or moldable partially collapsible chamber can be used to reproducibly control mixing patterns and shear rates for whole blood mixing with aggregation agonist(s) to achieve appropriate levels of platelet aggregation.

Once adequate mixing has occurred, the platelet aggregates formed in the whole blood are passed through a filter. This is done in the present embodiment simply by inverting the mixing/filtering chamber as shown in FIG. 3. Preferably, the mixing/filtering chamber is also stabilized in the manner previously described. Filtration can occur as gravity forces the blood through the filter 24 and into the stem 28 for removal. However, other methods can be used to cause flow across the filter as is desired. This flow can be created manually with a syringe, or by connecting to an evacuated chamber, or automatically with a help of a pump or linear actuator. Further, though not required, centrifugation can be used to increase the downward force through the filter and out through the stem. Optionally, a control valve 30 and a filter grid 26 can be used to optimize retention of platelet aggregates and effective removal of other blood components.

Filtered blood (devoid of aggregates) can then be collected in a holding receptacle. For example, a syringe 44 can be used for the holding receptacle. This blood can then be returned to the patient, stored (such as for generation of plasma or serum for use as a possible substrate), or disposed.

Once the non-aggregated portion of the blood has been removed, the filter with platelet aggregates can be rinsed with essentially room-temperature saline (15–25° C.) by manual or automated aspiration. In one embodiment, the saline solution can be injected using a syringe through the stem 28 that is controlled by the valve 30, or through stem 38. Such a rinsing or washing can remove trapped or otherwise present plasma, other blood cells, and/or residual traces of aggregating agent. The wash can then be collected in another waste container, such as another syringe, for disposal.

To collect or concentrate the platelets, the mixing/filtering chamber can then be soaked and aspirated manually or automatically, again through the stem 28 with appropriate fluid, e.g., physiological solution such as saline, plasma, or other isotonic salt solution, to deaggregate the growth factor-containing platelet aggregates. Deaggregated platelets can then be recovered in a collection receptacle, such as yet another syringe or other pump device, and thus, be made ready for use. The harvested platelet concentrate can be mixed with an adjuvant and delivered to the desired site.

Figure 4:
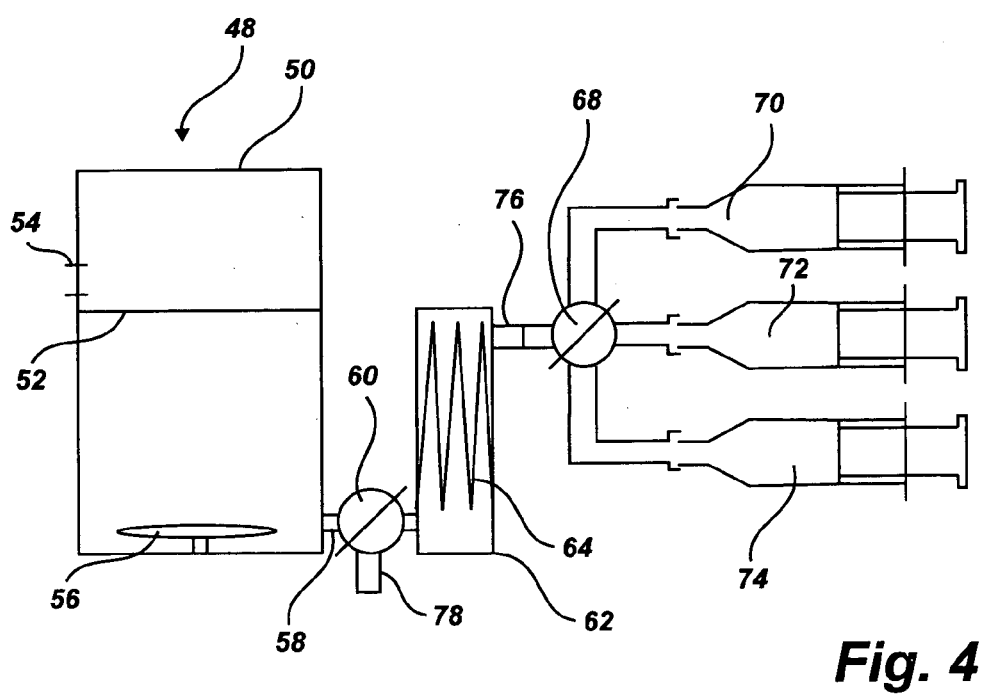
FIG. 4 is a schematic representation of an alternative embodiment of the present invention wherein the mixing and filtering chamber are separated by and valve.

Referring to FIG. 4, an alternative system, indicated generally at 48, is shown. In this embodiment, a mixing chamber 50 is filled with whole blood and an aggregating agent through an inlet port 54 to a desired blood level 52. A mixing mechanism 56, which in this case is a stirring bar, is present for mixing the whole blood with the aggregating agent. A conduit 58 is used to transport the aggregated whole blood from the mixing chamber 50 to a filtering chamber 62. A valve 60 is present to prevent flow through the conduit in one or both directions when flow is not desired. Once the aggregated whole blood is in the filtering chamber 62, it is pulled through a porous filter 64 having pore sizes and material properties as previously described, for example. In the present embodiment, the filter is in a pleated arrangement, providing increased surface area if desired. Aggregated platelets larger than a predetermined size will collect on the filter as residual whole blood components, e.g., plasma, leukocytes, erythrocytes, etc., are allowed to pass.

In the present embodiment, a series of syringes 70, 72, 74 having different purposes are present and attached to a filter port 76 through a valve 68. The valve 68 can be used to selectively utilize one of the syringes when desired. If a similar pump system such as provided the series of syringes 70, 72, 74 are desired for use between the mixing chamber 50 and the filter chamber 62, then a valve port 78 can be present as well.

In one embodiment, a first syringe 70 can be used to draw the whole blood through the mixing and filtering portions of the system 48. Ultimately, first syringe 70 is used to create the negative pressure desired for flow of the whole blood through the system 48. The first syringe 70 is also used to collect residual blood components not collected in the filter 64 as previously described. By turning valve 68 such that fluid communication between the second syringe 72 and the rest of the system 48 can be effected, an aspirating step can occur wherein the aggregated platelets collected in the filter can be cleaned, such as with saline or another physiological solution, as will be described more fully hereinafter. Still further, the valve 68 can be oriented for functionality of the third syringe 74. The third syringe 74 can be used to inject deaggregating agent into the filtering chamber 62, as will also be described hereinafter. Though the pumping, aspirating, and deaggregating systems shown in this embodiment is a syringe/valve system, other systems could also be used with similar success.

Though both of the device systems of FIGS. 1 to 4 have been described with respect to the separation of platelets from whole blood, other platelet suspensions could also be used. For example, the separation of platelets from platelet rich plasma and/or platelet packs could also benefit from the systems of the present invention.

A more fully automated substitute for either of the systems can be used where the blood filtration, washing, deaggregation, and cellular concentrate collection steps may be accomplished by automated inverting, valving, and aspiration steps controlled by a microprocessor and linear actuator, for example. A manual alternative for the semi-automated disposable device can also be implemented for use where the mixing of aggregating agonist with blood is accomplished by simply shaking or rotating a device, or via a plunger that is aspirated to move and mix the blood (with or without a stationary mixing grid), or using a motor-operated or spring-loaded stirring or agitation mechanism. The remainder of the process, i.e., filtration, washing, and retrieval (with or without de-aggregation) can be accomplished manually, or automatically, as would be known by one skilled in the art after reading the present disclosure.

The systems and methods of the present invention allow for the isolation of platelets from whole blood in a device (preferably without the use of a centrifuge) such that growth factors contained within the cells are retained. Underlying elements of the process can involve the isolation of platelets from whole blood by size-selective filtration of aggregated cells. Platelets are first aggregated by controlled mixing at specified temperature and time intervals with appropriate aggregating agents prior to separation by filtration. Platelet aggregates retained on a filter can then be deaggregated and recovered under conditions that preserve their growth factor content. Platelets, when combined with a substrate, provide a preparation with dispersed cells that can release growth factors on-site immediately and/or over an extended period of time.

In another embodiment, a method of stabilizing and healing an aneurysm can comprise the steps of (a) identifying an aneurysm sac; (b) providing a wound healant comprising isolated platelets suspended in the physiological solution, and a clinical carrier substrate configured for carrying the platelets; and (c) causing the wound healant to contact the aneurysm sac. The contact can occur by filling the sac with the wound healant, either fully or partially. Appropriate substrates can include coils or gels, for example. Additionally, seed cells can also be incorporated into the wound healant, including fibroblasts and smooth muscle seed cells.

The following preferred embodiments of another method of the present invention are provided, but are not meant to be limiting. Steps for obtaining and delivering concentrated platelets can include blood collection, platelet aggregation, separation of aggregates from blood, washing platelet aggregates to eliminate excess agonist and other cells, de-aggregation and collection of platelets, and delivery of platelets to a wound site.

Blood Collection

Therapeutic wound healing concentration requirements and related gel volume needs will dictate preoperative, intraoperative, or bedside blood collection of about 10 to 200 ml, based on anticipated need. The patient's blood can be collected via venapuncture into a container with pre-dispensed anticoagulant, e.g., sodium citrate. The patient's blood may be processed immediately or may be stored at room temperature for up to a few hours. The processing of the blood can begin as soon as from 10 to 15 minutes before growth factor delivery is desired, the timing being limited on the low end by the time it takes to carry out an effective separation and wound healant preparation.

Use of patient's fresh autologous blood is preferred, and is likely to result in the optimum wound healant for that patient. However, stored blood, e.g., from a blood bank, may be used, although blood stored for longer than 6 hours may carry the risk of lower platelet, and/or growth factor recovery.

Platelet Aggregation.

Once collected, the blood can be transferred to a processing device, such as one previously described. A first step in the process involves stimulating the platelets to form aggregates under controlled conditions. This can be achieved by the expulsion of prepackaged concentrations of platelet agonist into blood at a functional temperature followed by controlled mixing for a functional amount of time. Acceptable agonists for platelet aggregation can include thrombin, ristocetin, arachidonic acid, collagen, epinephrine, and ADP.

Though all of the above mentioned agonists are functional, their use in some circumstances may result in the release and loss of granular contents (such as growth factors), or have other adverse processing effects upon aggregation. This aside, certain positive characteristics may outweigh perceived negative affects. For example, collagen may be desired in specific circumstances where growth factors are preferably to be delivered in a collagen substrate. In one embodiment, the use of from $10\mu M$ to $100\mu M$ of ADP can be preferred for platelet aggregation. Both collagen and ADP have some inherent growth promoting features. In another embodiment, the use of collagen or epinephrine can be preferred for platelet aggregation.

Though any functional temperature and mixing time can be used, preferred temperatures for aggregation can be from 15° C. to 42° C., and a more preferred temperature range can be from 20° C. to 37° C. Preferred mixing times can be from 15 to 300 seconds, and more preferred mixing times can be from 60 to 180 seconds. If a stir bar is used for mixing, any functional RPM rate can be used, though from 60 to 3000 RPMs provides a range, and from 200 to 1000 1500RPMs provides a preferred range for stirring. This speed may vary depending on the geometry of the mixing chamber and geometry of the stir bar. The temperature, time, and stirring force for mixing can be optimized with respect to a specific system, as would be ascertainable by one skilled in the art after reading the present disclosure. In one embodiment, these parameters can be optimized to create platelet aggregates with nominal dimensions of over approximately 15 $\mu$m for eventual filtration.

The platelet aggregation process should not be allowed to proceed beyond specific time points (typically, 3 minutes or less) dependent upon the aggregating agent utilized. Controlling the elapsed time for aggregation can minimize the risk of growth factor leakage. For example, as disclosed in Mohammad S F, *Am J Pathol.* 79: 81–94. 1975, a lower aggregation time may be preferred by restricting cell aggregation to the first phase of aggregation (for ADP aggregation), and interrupting the process before the second phase of aggregation (the stage during which platelet granular contents are released). Conducting the aggregation process at room temperature, or at temperatures less than 37° C., may also provide some protection against over-aggressive aggregation of platelets that could lead to release of granular contents (such as growth factors) that may occur at higher temperatures, e.g., 37° C. However, this could potentially reduce the efficiency of the aggregating process leading to slightly lower yields of platelets compared with aggregation at 37° C. Mixing dynamics of agonist and blood should also be considered for controlled aggregation. If mixing is too gentle, all single platelets may not aggregate. If mixing is too aggressive, high shears and violent collisions may disrupt formed aggregates, thus damaging the cells and releasing the cytoplasmic contents including growth factors. Optimal ranges of time of aggregation (~1 to 3 minutes), temperature (22° C. to 37° C.), and mixing, e.g. rotational speeds in the order of 200 to 1500 RPM for proper mixing accomplished by a stir-bar in a cylindrical cup-like chamber, that results in maximum aggregation of platelets and minimum loss of growth factors are desired.

Separation of Aggregates from Blood

After agonist mixing is stopped, blood with cellular aggregates is immediately passed through a filter assembly e.g. filter(s) of single or multiple stages with nominal pore size(s) between 15 and 500 $\mu$m. Though pore sizes from 100 to 500 $\mu$m are functional, preferably, the pore size can be from 15 to 100 $\mu$m. This being said, any pore size that allows for the retention of cell aggregates and passage of single blood cells and plasma is considered functional.

Washing Platelet Aggregates to Eliminate Excess Agonist and Cells

Aggregates retained on the filter may be rinsed with wash fluid, such as room-temperature saline, to remove residual agonist, plasma proteins, and loosely trapped cells, leaving behind the aggregated platelets. The washing fluid can be of any functional temperature and of any functional pH. However, the temperature is preferably from 15° C. to 30° C., and more preferably from 18° C. to 25° C. The pH level of the washing fluid can be from 5.5 to 8, but is preferably from 6 to 8.

Deaggregation and Collection of Platelets

In a preferred process, deaggregation can be carried out for platelet aggregates captured in the filter assembly. This allows for subsequent dispersion of cells or small aggregates in a desired medium when the cells are delivered to a wound site. Deaggregation, and the conditions under which it is carried out, may also lead to effective retention of growth factors inside the cells, as the aggregation process is reversed before degranulation ensues. Deaggregation may also result in higher cell yields because retrieval of deaggregated cells may be less demanding and more efficient than removing filter-bound intact aggregates.

To reverse aggregation, aggregates captured on the filter can be soaked in a specified volume of a medium of a desired functional temperature and pH. Such appropriate deaggregating mediums can include saline, ACD-saline, or other salt solutions with additives to facilitate deaggregation, e.g., apyrase, aspirin, IIb/IIIa antagonists, other platelet function suppressors, plasma, albumin, or the like. This can be accompanied by frequent mixing, e.g., aspiration with a syringe, and/or agitation, e.g., vibration, for a functional time period to facilitate deaggregation and producing single cells or small aggregates. Preferred temperature for this process can be from 18° C. to 42° C., with more preferred temperatures being from 33° C. to 37° C. Preferred pH levels can be from 5.5 to 8, with a more preferred pH range from 6 to 8. Any functional time for deaggregation can be implemented, though from 30 to 1000 seconds is considered to be preferred, with from 30 to 300 seconds being more preferred.

In an alternative embodiment, by aggressive aspiration, cell aggregates can be separated and recovered without deaggregation within the sealed filter compartment, followed by retrieval of both bound and expelled growth factors.

In another embodiment, aggregates may be left on the filter, platelet growth factors expelled from the aggregates by any means known, e.g., degranulation, and collected in a desired volume for delivery to the wound site.

Delivery of Platelet Concentrates to the Wound Site

The suspensions obtained from this process may be combined with a wide variety of clinical wound treatment adjuvant substrates for delivery to the wound site. Specific substrate properties can be selected to tailor growth factor delivery to promote healing in soft, hard, and/or connective tissue. The concentrated growth factor-laden cells or solutions from this process can readily be combined intraoperatively with a variety of dressing and delivery substrates including: hydrogels, hyaluronic acid, gelatins, fibrin and fibrinogen, collagen, alginate, albumin, chitosan and other sponges, surgical foams, plasma or serum along with antimicrobials and pharmaceuticals, etc.

EXAMPLES

The following example illustrates a preferred embodiment of the invention that is presently known. However, other embodiments can be practiced that are also within the scope of the present invention.

Example 1

Separation of Platelets from Whole Blood

A separation of platelets from whole blood was carried out by the following process: About 10 ml of whole blood was collected from 4 human subjects by venapuncture into a syringe having a predispensed anticoagulant contained therein. To the collected whole blood was added 100 μM of ADP as an aggregating agent. The whole blood and aggregate combination was mixed in a chamber with a stir bar for 90 sec at 37° C. Once mixing was stopped, the blood with cellular aggregates was filtered through a filter assembly having pore sizes ranging from 20 μm to 100 μm under negative pressure exerted by a syringe. The filtered aggregates were washed with 30 ml of 18° C. saline for 1 minute. Next, the washed aggregates were incubated with a saline-ACD solution at 37° C. with gentle aspiration for 3–5 minutes. The saline-ACD solution having substantially deaggregated growth-factor containing platelets were then collected as a suspension.

Specifically, to assess the potential effectiveness of the above process of isolation of platelets, the following experiments were conducted: the yield of platelets harvested from human blood was determined and quantified (Example 2); aspects of the functional integrity of the platelets was determined (Example 3); and the presence of one of the most recognized growth factors, PDGF-AB, as a representative growth factor was determined (Example 4).

Example 2

Determination of Platelet Yield

Figure 5:
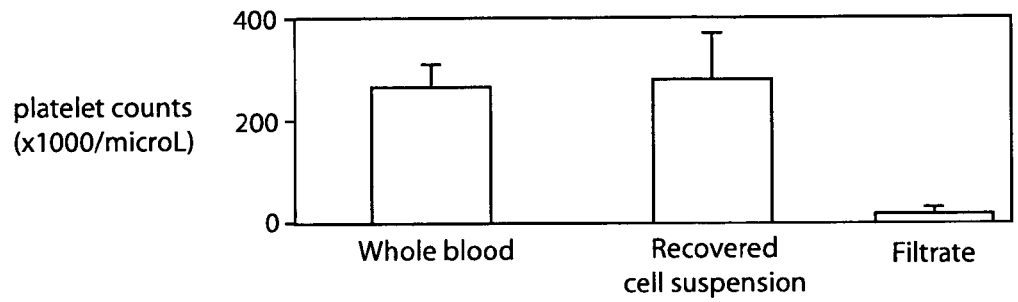
FIG. 5 is a graphical representation showing a hemocytometer count of platelet yield of a recovered cell suspension compared to whole blood and filtrate.

A platelet recovery assay was performed by placing a dilution of a platelet suspension, prepared in accordance with Example 1, in a hemocytometer where the number of platelets were counted using a phase contrast microscope or with the help of an electronic particle counter. Platelets recovered were compared with platelets recovered using a conventional centrifugation method of the prior art. Hemocytometer counts showed near complete recovery of platelets using the aggregation, filtration, and deaggregation method of the present invention. The results were quantified and are shown in FIG. 5. The waste filtrate from this process contained very few platelets in all cases indicating that aggregation and filtration process was very efficient in harvesting platelets from whole blood. It is worth noting that two of the four subjects that were part of this study were taking aspirin and/or calcium channel blockers (as antihypertension medication). Aspirin is a known suppressor of platelet aggregation, but platelets aggregated well using the methods described in the present invention and good recovery was observed. This being said, some patients with severe platelet deficiencies, or thrombocytopenia, or patients using potent platelet antagonists may not be preferred candidates for this process because their platelet counts may be too low or their functional integrity may be compromised. Such candidates may benefit more from platelets collected from a blood donor.

Example 3

Determination of Functional Integrity

Figure 6:
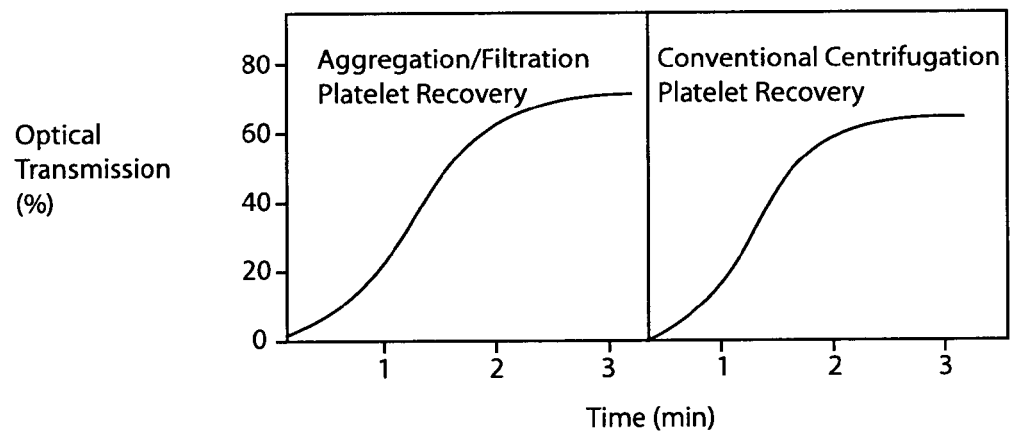
FIG. 6 is a graphical representation comparing function of platelets recovered by the aggregation/filtration process of the present invention and function of platelets recovered using a conventional centrifugation technique of the prior art.

To assess functional integrity, platelets recovered in accordance with Example 1 were added to autologous platelet poor plasma, incubated for 15 minutes at 37° C., and the function of platelets assessed in a BIO/DATA turbidometric platelet aggregometer using 50 μM of ADP as the aggregating agent. Platelets recovered by the present invention were compared with platelets in platelet rich plasma obtained by conventional centrifugation. The comparison of platelet function in a turbidometric aggregometer showed virtually identical platelet aggregation profiles between the platelets recovered by centrifugation, and those recovered by the present invention. FIG. 6 depicts these results. This suggests that the functional integrity of harvested and concentrated platelets obtained by the process of the present invention was not compromised when compared to a prior art method.

Example 4

Determination of Presence of PDGF-AB

Figure 7:
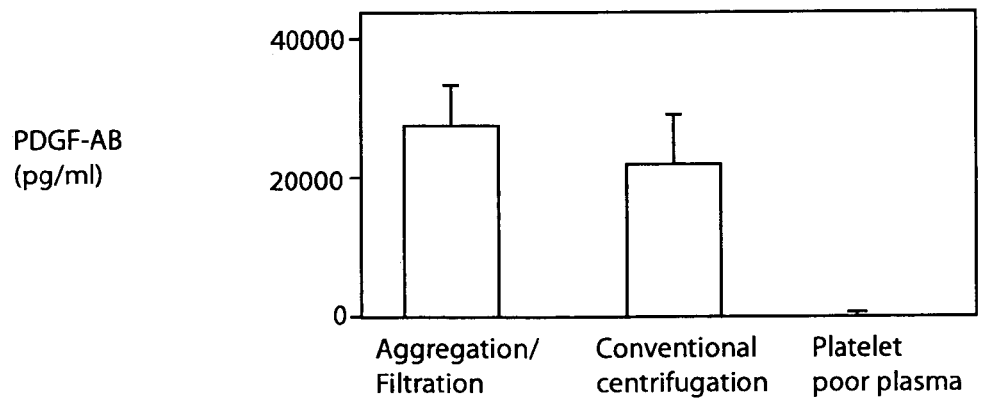
FIG. 7 is a graphical representation comparing PDGF-AB recovery from the aggregation/filtration process of the present invention and PDGF-AB recovery using a conventional centrifugation technique of the prior art.

To determine platelet-derived growth factor (PDGF-AB) presence in platelets concentrated as in Example 1, a chromogenic ELISA method (Quantikine, R&D systems) was utilized. Concentrated platelets obtained by the centrifugation method served as the reference (control) for valid comparisons. Functional viability of the growth factors contained in recovered platelets was assessed by measuring enhancement of human aortic smooth muscle cell proliferation. ELISA results indicated preservation of PDGF-AB in platelets recovered by this process similar to that of PDFG-AB from platelets recovered by centrifugation, as is shown in FIG. 7. This suggests that process steps outlined herein ensure that internal contents of the dense granules in the platelets, e.g., growth factors, are not substantially expelled. The negative control (platelet poor plasma) expressed virtually no PDGF-AB, which suggests valid experimental conditions. The full recovery of PDGF-AB in the platelets harvested by a process of the present invention indicates that other growth factors (PDGF-AA, TGF, VEGF, FGF, etc.) contained in platelets may likewise be preserved during the recovery process.

Example 5

Delivery of Platelet Concentrates to Smooth Muscle Cells

The platelet suspension derived by the method of Example 1 enhanced human aortic smooth muscle cell proliferation by 24% compared with the blank buffer control. The results were obtained from two subjects with samples analyzed in triplicate with a MTT assay.

It is to be understood that the above-referenced arrangements are only illustrative of the application for the principles of the present invention. Numerous modifications and alternative arrangements can be devised without departing from the spirit and scope of the present invention while the present invention has been shown in the drawings and fully described above with particularity and detail in connection with what is presently deemed to be the most practical and preferred embodiments(s) of the invention, it will be apparent to those of ordinary skill in the art that numerous modifications can be made without departing from the principles and concepts of the invention as set forth in the claims.

What is claimed is:

1. A method for separating platelets from whole blood, comprising:
    providing whole blood including platelets, leukocytes, erythrocytes, and blood plasma;
    selectively aggregating the platelets using an aggregating agent to form platelet aggregates that are larger in size than said leukocytes and said erythrocytes; and
    separating and recovering the platelet aggregates from the leukocytes, erythrocytes, and blood plasma, wherein the separating step comprises a filtering step.

2. A method as in claim 1, wherein the platelet aggregates are washed with an isotonic solution after the separating step.

3. A method as in claim 1, wherein the platelet aggregates are at least partially deaggregated after the separating step.

4. A method as in claim 1, wherein the platelet aggregates are suspended in a physiological isotonic solution after the separating step.

5. A method as in claim 3, wherein the deaggregated platelets are concentrated to a therapeutic level for delivery to a wound site.

6. A method as in claim 1, wherein the separating step is carried out without the use of centrifugation.

7. A method as in claim 1, wherein the separating step further comprises a sedimentation step.

8. A method as in claim 1, wherein the aggregating agent is selected from the group consisting of thrombin, ristocetin, arachidonic acid, collagen, epinephrine, adenosine di-phosphate, and combinations thereof.

9. A method as in claim 8, wherein the aggregating agent is adenosine di-phosphate.

10. A method as in claim 2, wherein the platelets are washed with a physiological solution at a temperature from about 18° C. to 25° C. and for about 1 to 3 minutes to remove residual components including agonists, red blood cells, white blood cells, and plasma proteins.

11. A method as in claim 1, further comprising the steps of aspirating the platelet aggregates after separation with physiological solution to deaggregate and resuspend the platelets while minimizing degranulation, thereby recovering single cells or small cell aggregates, said physiological solution being configured to preserve growth factors of the platelets.

12. A method as in claim 11, wherein the aspirating step is carried out with plasma.

13. A method as in claim 11, wherein the aspirating step is carried out using a member selected from the group consisting of ACD-saline and albumin solution.

14. A method as in claim 11, wherein the aspirating step occurs under controlled temperatures from 33° C. to 37° C., and at a pH from about 6 to 8.

15. A method as in claim 1, wherein the step of filtering is conducted with a biodegradable filter, and the step of recovering includes placing the filter with recovered platelets directly on a wound site.

16. A method as in claim 15, wherein the biodegradable filter comprises a material selected from the group consisting of polyglycolic acid, polylactic acid, polypeptide, collagen, and combinations thereof.

17. A method as in claim 1, wherein the separation occurs within 14 minutes for planned or emergency reinfusion or transfusion of the platelet.

18. A method as in claim 1, wherein the step of selectively aggregating the platelets is enhanced by mixing the whole blood and the aggregating agent at a temperature from 20° C. to 37° C. for about 60 to 180 seconds.

19. A method for separating platelets from a platelet suspension, comprising:

selectively aggregating the platelets using an aggregating agent to form platelet aggregates; and separating and recovering the platelet aggregates from the platelet suspension wherein the separating step comprises a filtering step.

20. A method as in claim 19, wherein the separating step occurs without centrifugation.

21. A method as in claim 19, wherein the aggregating agent is selected from the group consisting of thrombin, ristocetin, arachidonic acid, collagen, epinephrine, adenosine di-phosphate, and combinations thereof.

22. A method as in claim 19, wherein the platelet aggregates are washed with a physiological solution after filtration.

23. A method as in claim 19, wherein the platelet aggregates are at least partially deaggregated after filtration.

24. A method as in claim 20, wherein the platelet aggregates are suspended in a physiologically neutral solution after filtration.

25. A method as in claim 19, wherein the platelet suspension is platelet rich plasma.

26. A method as in claim 19, wherein the platelet suspension is whole blood.

27. A method as in claim 19, wherein the platelet suspension is a platelet pack.

28. A method as in claim 1, wherein the recovering is carried out such that the platelet aggregates are substantially intact.

* * * * *